United States Patent
Yao

(10) Patent No.: US 9,699,294 B1
(45) Date of Patent: Jul. 4, 2017

(54) MOBILE SMART MASSAGE DEVICE

(71) Applicant: Chun-Fu Yao, Taipei (TW)

(72) Inventor: Chun-Fu Yao, Taipei (TW)

( * ) Notice: Subject to any disclaimer, the term of this patent is extended or adjusted under 35 U.S.C. 154(b) by 0 days.

(21) Appl. No.: 15/173,715

(22) Filed: Jun. 5, 2016

(51) Int. Cl.
| H04B 1/38 | (2015.01) |
| H04M 1/725 | (2006.01) |
| A61N 1/36 | (2006.01) |
| A61N 1/04 | (2006.01) |
| A61H 39/00 | (2006.01) |
| A61H 39/06 | (2006.01) |

(52) U.S. Cl.
CPC ...... *H04M 1/72533* (2013.01); *A61H 39/002* (2013.01); *A61H 39/06* (2013.01); *A61N 1/0452* (2013.01); *A61N 1/36021* (2013.01); *A61H 2201/501* (2013.01); *A61H 2201/5035* (2013.01); *A61H 2201/5046* (2013.01)

(58) Field of Classification Search
CPC .............................................. H04M 1/72533
USPC ....................................................... 455/557
See application file for complete search history.

(56) References Cited

U.S. PATENT DOCUMENTS

| 4,827,939 | A | * | 5/1989 | Cartmell | A61B 5/04087 600/392 |
| 5,150,708 | A | * | 9/1992 | Brooks | A61N 1/046 600/391 |
| 8,689,647 | B2 | * | 4/2014 | Stein | A61B 5/4528 73/777 |
| 9,107,644 | B2 | * | 8/2015 | Frix | A61B 5/721 |
| 9,339,236 | B2 | * | 5/2016 | Frix | A61B 5/14551 |
| 2011/0166491 | A1 | * | 7/2011 | Sankai | A41D 13/1281 601/84 |

* cited by examiner

*Primary Examiner* — April G Gonzales

(57) ABSTRACT

A mobile smart massage device includes a mobile device having a first connector; a connective wire having one end installed with a second connector connectable to the first connector of the mobile device and another end thereof being installed with a plurality of conductive connecting units each capable of being connected with a conductive adhering sheet; and a chip control module installed on the second connector of the connective wire for determination of connection coupling and for data transmission. The conductive adhering sheet is installed with a connecting portion for connecting with the conductive connecting unit. The and second first connector of the mobile device is one of a USB 2.0 socket, a USB3.0 socket, a MICRO USB plug and an AUDIO JACJ plug. The mobile device is installed with an application program which may be a mobile application.

4 Claims, 3 Drawing Sheets

_US 9,699,294 B1_

MOBILE SMART MASSAGE DEVICE

FIELD OF THE INVENTION

The present invention relates to massage devices, and in particular to a mobile smart massage device.

BACKGROUND OF THE INVENTION

A prior electric treatment machine is widely used in treatment of aches and recover of human body. The main structure thereof has an electrode sheet which can emit electric wave with proper waveform, amplitude and frequency for stimulating the portion of the sicker to be treated. For a sicker necessary to be monitored for a long time, he (or she) needs to a hospital for electric treatment.

A current used electric treatment machine is huge and thus is inconvenient to be carried out. Meanwhile, it occupies a large space for installation. Therefore this kind of prior electric treatment machine is not suitable to be placed in house. For improving the defect in the prior art structure, small size electrical treatment machine is developed. Although these kinds of electrical treatment machine only occupies less space and is easily portable, it must sold individually, while it is expensive and is inconvenient in portability.

SUMMARY OF THE INVENTION

Accordingly, object of the present invention is to provide a mobile smart massage device, in that a mobile device having a first connector and a connective wire having one end installed with a second connector connectable to the first connector of the mobile device and another end thereof being installed with a plurality of conductive connecting units each capable of being connected with a conductive adhering sheet. Furthermore, a chip control module installed on the second connector of the connective wire for determination of connection coupling and for data transmission. Therefore it can be controlled easily and conveniently.

To achieve above object, the present invention provide a mobile smart massage device comprising: a mobile device having a first connector; a connective wire having one end installed with a second connector connectable to the first connector of the mobile device and another end thereof being installed with a plurality of conductive connecting units each capable of being connected with a conductive adhering sheet; and a chip control module installed on the second connector of the connective wire for determination of connection coupling and for data transmission.

The conductive adhering sheet is installed with a connecting portion for connecting with the conductive connecting unit. The connecting portion is an insertion unit or a buckle.

The mobile phone is one of a smart phone, a tablet computer, and a notebook computer. The mobile device is installed with an application program (APP).

BRIEF DESCRIPTION OF THE INVENTION

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims.

Figure 1:
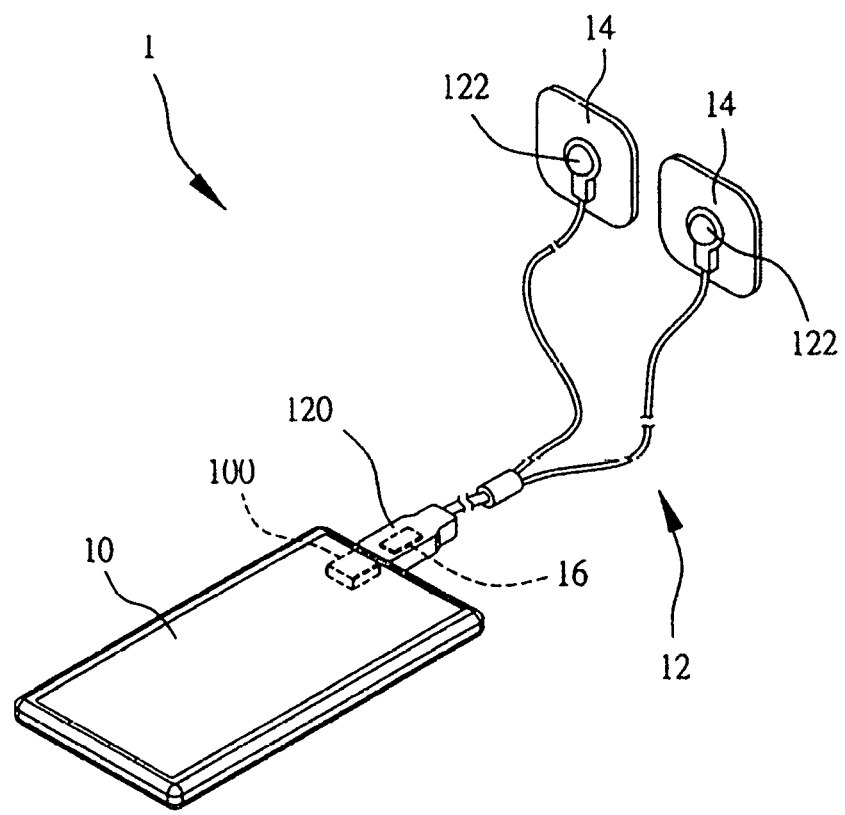
FIG. 1 is a schematic view about the preferred embodiment of the present invention.
Figure 2:
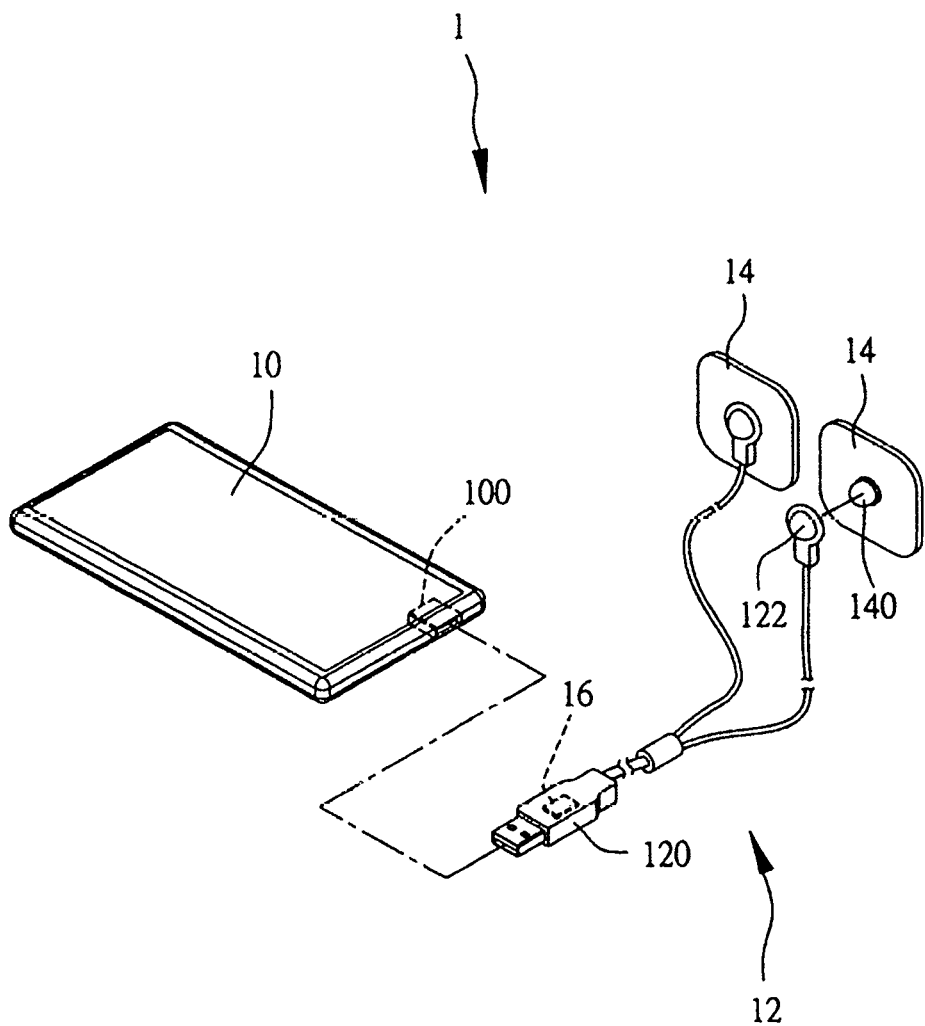
FIG. 2 is an assembled schematic view of the preferred embodiment of the present invention.

With reference to FIGS. 1 and 2, the structure of the present invention is illustrated with respective to the schematic view and perspective view as shown. The present invention includes the following elements.

A mobile device 10 is installed with a first connector 100.

A conductive wire 12 has one end installing with a second connector 120 and another end thereof installing with a plurality of conductive connecting units 122.

A plurality of conductive adhering sheet 14 is included. Each conductive adhering sheet 14 is installed with a connecting portion 140 which is used to connect the conductive connecting unit 122 of the conductive wire 12 so as to complete the assembly work. The connecting portion 140 may have a form of an insertion unit or a buckle with respective to the conductive connecting unit 122 having a form of an insertion hole or a buckling unit, respectively.

In above description, the mobile device 10 is one of a smart phone, a plate computer or a notebook computer. Therefore, the conductive wire 12 may be connected to the first connector 100 of a smart phone, a plate computer or a notebook computer. At this situation, the conductive wire 12 is electrically connected to the conductive adhering sheet 14. A chip control module 16 is installed on a matched connector 120 for being coupled to the connector 100 and then data transmission. The first connector 100 may be a USB 2.0 socket, a USB3.0 socket, a MICRO USB plug or a AUDIO JACJ plug.

Figure 3:
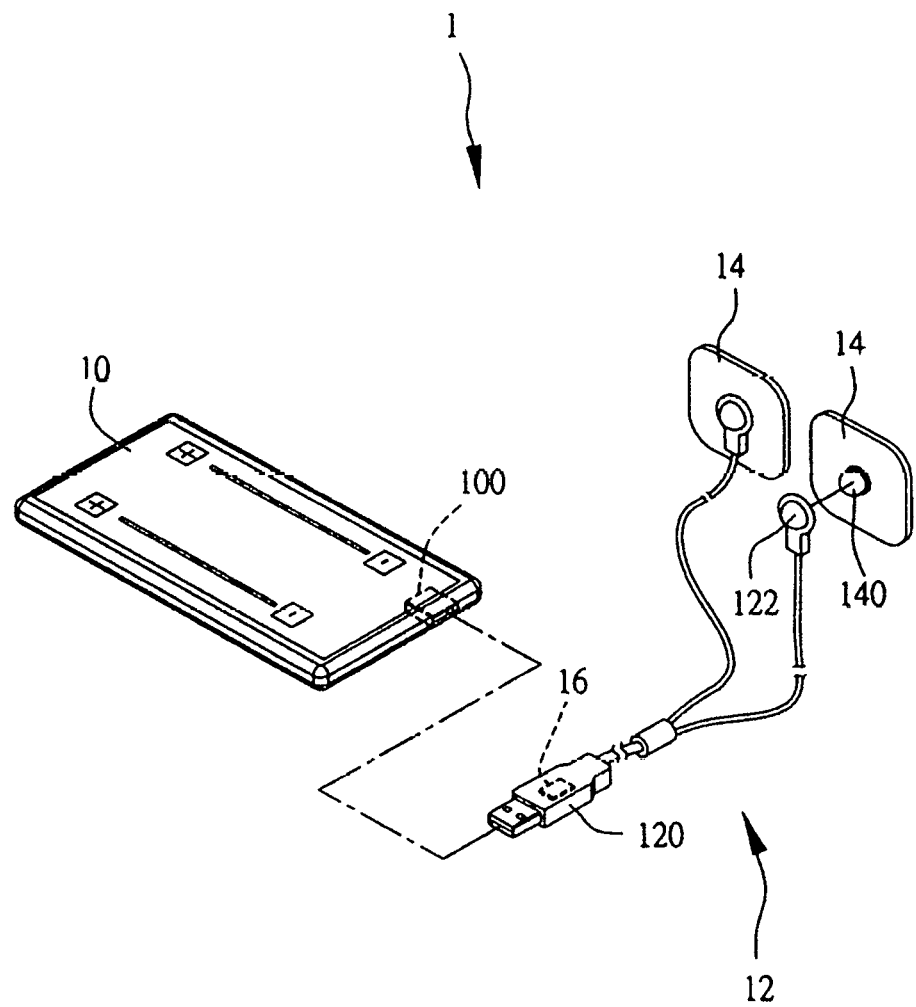
FIG. 3 is a schematic view showing the application of the present invention.

In using, the conductive connecting unit 122 is connected to the connecting portion 140 so that the conductive connecting unit 122 and the conductive adhering sheet 14 are conductive. Then the matched second connector 120 is inserted into the first connector 100. With reference to FIG. 3, a preferred embodiment about the use of the present invention is illustrated. After assembling of the mobile phone 14, the connective wire 12 and the conductive adhering sheet 14, the mobile phone 10 is installed with an application program (being a mobile application, APP), than the device can be initiated. By this APP, the operation mode, time period and strength of the electrical treatment (massage) may be selected. The mode may be one of massage, skin-scraping therapy, acupressure, acupuncture and moxibustion, beating, etc., and other operation modes. The left side of the modes is bar for time adjustment, and at the right side is a strength bar. Thereby, the user can operate the present invention easily. The electrical treatment can be performed by operation in the mobile phone. The user can operate the present invention easily and conveniently by only carrying a conductive wire.

It should be noted that the connector 100 in the mobile phone 10 has the function of OTG (abbreviation of On-The-Go), generally, it is called as USB OTG which is a standby standard of USB 2.0. Since the connective wire 12 is installed with the chip control module 16 which is on the connector 120, so that the USB can be connected to the connector 12 for judging and data reading. No computer is used for control, while the operation is performed directly. Thereby, the connective wire 12 with the chip control module 16 is used to connect with the connector 100 in the mobile phone 10 for current transmission so that the present invention can be carried convenient and carried easily.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A mobile smart massage device comprising:

a mobile device (10) installed with a first connector (100);

a conductive wire (12) having one end installing with a second connector (120) and another end thereof installing with a plurality of conductive connecting units (122); the second connector (120) of the conductive wire (12) being connectable to the first connector (100) of the mobile device (10);

a plurality of conductive adhering sheet (14); each conductive adhering sheet (14) being installed with a connecting portion (140) which is used to connect the conductive connecting unit (122) of the conductive wire (12); the connecting portion (140) has a form of an insertion unit or a buckle with respective to the conductive connecting unit (122) having a form of an insertion hole or a buckling unit, respectively;

wherein the conductive wire (12) is electrically connected to the conductive adhering sheet (14); a chip control module (16) is installed on a matched connector (120) for being coupled to the first connector (100) of the mobile device (10) and then data is transmitted; and the mobile device (10) is installed with an application program; by this APP, the operation mode, time period and strength of the electrical treatment are selectable; the mode is one of operation modes selected from massage, skin-scraping therapy, acupressure, acupuncture and moxibustion, and beating; and thus, electrical treatment is performed by the selected operation.

2. The mobile smart massage device as claimed in claim 1, wherein the mobile device is one of a smart phone, a tablet computer, and a notebook computer.

3. The mobile smart massage device as claimed in claim 1, wherein the first connector of the mobile device is one of a USB 2.0 socket, a USB3.0 socket, a MICRO USB plug and an AUDIO JACJ plug.

4. The mobile smart massage device as claimed in claim 1, wherein the second connector of the connective wire is one of a USB 2.0 socket, a USB3.0 socket, a MICRO USB plug or an AUDIO JACJ plug.

* * * * *